US012580404B2

(12) United States Patent
Price et al.

(10) Patent No.: US 12,580,404 B2
(45) Date of Patent: Mar. 17, 2026

(54) APPARATUSES, SYSTEMS, AND METHODS FOR PROVIDING A TWO-WIRE SENSOR DEVICE

(71) Applicant: Schneider Electric Buildings Americas, Inc., Carrollton, TX (US)

(72) Inventors: Wray Robert Price, Tigard, OR (US); Girish Thorat, Montreal (CA); Richard Nathan Dinsdale, Vancouver, WA (US)

(73) Assignee: Schneider Electric Buildings Americas, Inc., Carrollton, TX (US)

( * ) Notice: Subject to any disclaimer, the term of this patent is extended or adjusted under 35 U.S.C. 154(b) by 308 days.

(21) Appl. No.: 18/138,202

(22) Filed: Apr. 24, 2023

(65) Prior Publication Data

US 2023/0344256 A1     Oct. 26, 2023

Related U.S. Application Data

(60) Provisional application No. 63/334,431, filed on Apr. 25, 2022.

(51) Int. Cl.
| | |
|---|---|
| *G01N 27/00* | (2006.01) |
| *G01N 33/00* | (2006.01) |
| *H02J 7/00* | (2006.01) |

(52) U.S. Cl.
CPC ........ *H02J 7/0063* (2013.01); *G01N 33/0009* (2013.01); *H02J 2207/20* (2020.01); *H02J 2207/50* (2020.01)

(58) Field of Classification Search
None
See application file for complete search history.

(56) References Cited

U.S. PATENT DOCUMENTS

| | | | |
|---|---|---|---|
| 6,208,254 B1 * | 3/2001 | McQueen | G01F 1/6847 73/204.25 |
| 10,352,807 B2 | 7/2019 | Soennichsen | |
| 2004/0180791 A1 * | 9/2004 | Cass | A01K 85/01 43/42.31 |
| 2009/0015216 A1 * | 1/2009 | Seberger | H02M 3/155 323/234 |

* cited by examiner

*Primary Examiner* — John E Breene
*Assistant Examiner* — Alex T Devito
(74) *Attorney, Agent, or Firm* — FIG. 1 Patents

(57) ABSTRACT

Apparatuses, systems, and methods are described for providing a sensor device. The system includes a control unit and a sensing unit. The sensing unit is coupleable to the control unit via a current loop and includes an input terminal coupleable to the current loop, at least one energy storage unit configured to be charged to a first voltage from the input terminal, a sensing element configured to sense an environmental parameter, wherein the sensing element receives power from the at least one energy storage unit at a second voltage, and wherein the second voltage is lower than the first voltage, a controller configured to receive a sensor signal from the sensing element and to generate an output signal, and an output terminal coupleable to the current loop and configured to transmit output corresponding to the output signal to the control unit via the current loop.

20 Claims, 5 Drawing Sheets

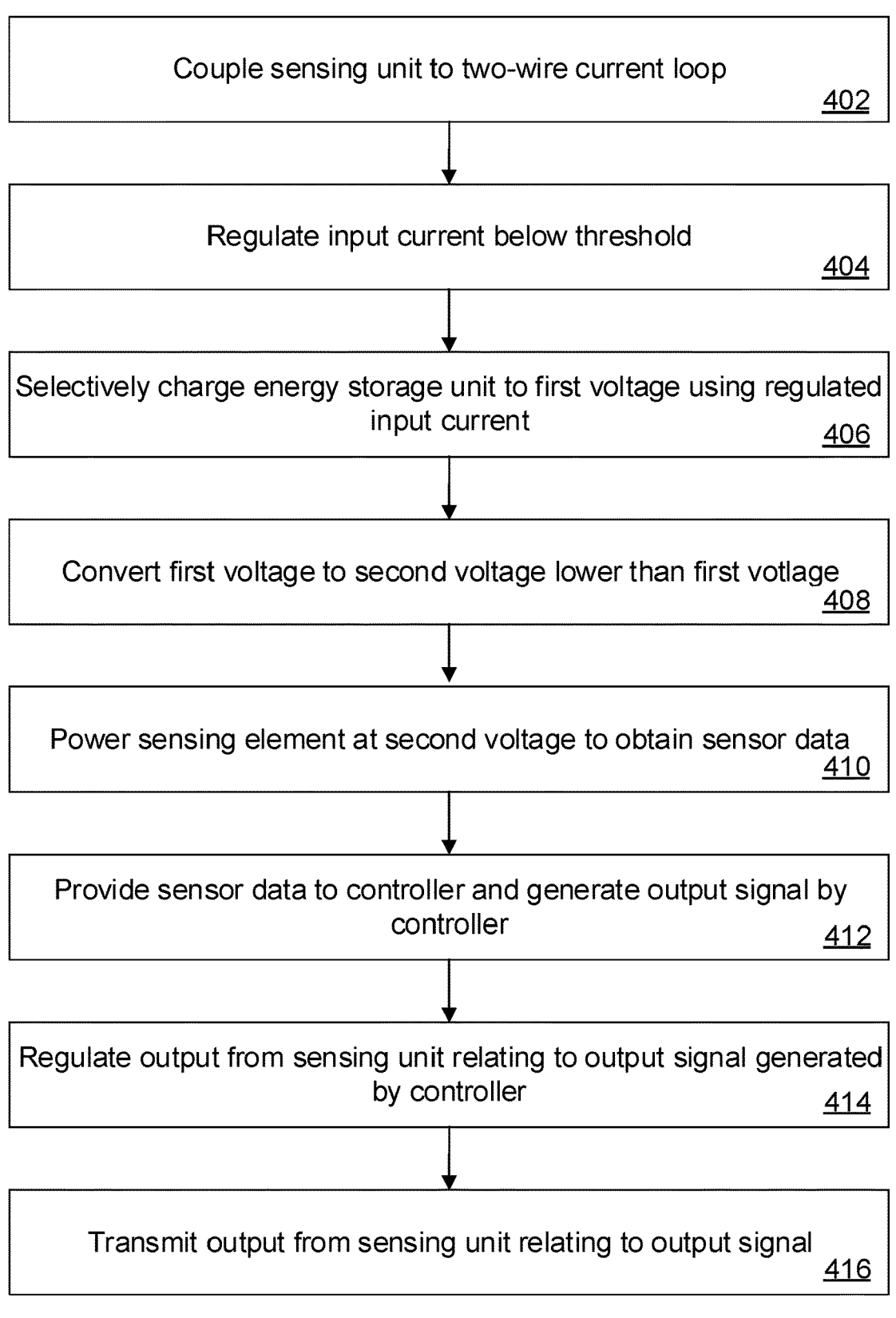

Couple sensing unit to two-wire current loop
402

Regulate input current below threshold
404

Selectively charge energy storage unit to first voltage using regulated input current
406

Convert first voltage to second voltage lower than first votlage
408

Power sensing element at second voltage to obtain sensor data
410

Provide sensor data to controller and generate output signal by controller
412

Regulate output from sensing unit relating to output signal generated by controller
414

Transmit output from sensing unit relating to output signal
416

APPARATUSES, SYSTEMS, AND METHODS FOR PROVIDING A TWO-WIRE SENSOR DEVICE

RELATED APPLICATION

The present application claims priority to U.S. Provisional Patent Application Ser. No. 63/334,431, filed on Apr. 25, 2022, and entitled APPARATUSES, SYSTEMS, AND METHODS FOR PROVIDING A TWO-WIRE SENSOR DEVICE, which is incorporated by reference herein in its entirety.

TECHNICAL FIELD

The present disclosure relates to sensor devices, and more particularly to providing sensor devices capable of being coupled to a two-wire current loop.

BACKGROUND

Some sensors require high peak current to operate, for example to power sensor components thereof and/or to communicate signals relating to data obtained by the sensor component(s). However, there may be limitations on how much current may be obtained via a current loop coupled to the sensor(s), resulting in the current loop being unable to both provide power for the sensor and to also obtain readable data from the sensor via the current loop. For example, on a 4-20 milliamp (mA) current loop, a sensor cannot draw more than 4 mA from a power supply when only two wires are connected to the sensor, where one wire is the power supply and the second wire is the reading output. If more than 4 mA is drawn by the sensor through the power supply wire, more than 4 mA must be outputted through the reading-output wire. This leads to the reading output being unable to differentiate the sensor reading from the current drawn by the sensors. Some sensors, such as described in U.S. Pat. No. 10,352,807, assigned to VERIS INDUS-TRIES, LLC, may receive power from a 4-20 mA current loop and include a capacitor charged to a low supply voltage used by a microcontroller (e.g., 3.3V). However, charging a capacitor only to a low voltage associated with a microcontroller may reduce overall efficiency and useability in a system having a sensor which has a high peak current draw.

SUMMARY

Implementations consistent with the present disclosure may provide numerous benefits, such as enabling high peak current sensors to be used with two-wire current loops while being able to properly obtain sensor output data on the reading output wire. For example, according to various aspects of the present disclosure, provided is a two-wire sensing unit (e.g., environmental sensor such as a carbon dioxide ($CO_2$) sensor) coupleable to a 4-20 milliamp (mA) loop-used to measure an environmental parameter in a space.

Various sensing units, such as those involving environmental (e.g., $CO_2$) sensors, may utilize high peak current to operate, measuring a $CO_2$ value and relaying this information over the 4-20 mA current loop may be a challenge due to minimum operational requirement(s) of the loop current of 4 mA. Implementations consistent with the present disclosure may assist to manage the overall power supply using a low power controller and one or more appropriate capacitive banks. Loop-powered devices may help to reduce install time (e.g., by virtue of less wiring) and enable robust usage in noisy environments.

In various systems, such as an air-quality-sensing system, there might exist a need to power one or more sensors (e.g. $CO_2$ sensor(s) or other high peak current sensor(s)) with more than 4 mA via a respective 4-20 mA current loop but cannot draw more than 4 mA from an associated power supply when only two wires are connected to the sensing unit. One wire of the two-wire current loop may correspond to the power supply, while the second wire may be associated with the reading output. If more than 4 mA is drawn for a sensor through the power-supply wire for a respective current loop, more than 4 mA must be outputted through the respective reading-output wire as a result. Implementations consistent with the present disclosure provide that the reading-output signal may be configured to remain independent of the current drawn by the sensor(s). Otherwise, a Building Automation System (BAS) receiving the reading output might be unable to differentiate the sensor reading from the current drawn by the sensor(s). In contrast to existing systems, implementations consistent with the present disclosure may enable powering sensing units with more than 4 mA in two-wire 4-20 mA systems without outputting more than 4 mA through the reading-output wire.

Implementations consistent with the present disclosure may enable managing peak current demand of a sensor, such as an environmental (e.g., $CO_2$) sensor keeping the loop performance of 4-20 mA. Additional advantages may be provided by enabling an efficient power supply design and feedback system to a controller to ensure continuous operation. Still further advantages may be obtained in relation to low power management of a controller. According to aspects of the present disclosure, the loop current may be limited using a shunt regulator to always maintain the loop performance (e.g., at a fixed 4 mA current). One or more appropriate capacitors, capacitor banks, and/or energy storage units may be determined, designed, and/or pre-selected to support a peak demand of one or more sensing units. An efficient DC-DC power supply may be provided to ensure maximum power harvesting through capacitors. Feedback to a controller regarding an input state to the power supply may be provided to ensure continuous operation. A controller may be configured to operate in a low power mode by managing the sensor operation According to aspects of the present disclosure, provided is a sensing unit to sense an environmental parameter. The sensing unit may include an input terminal, at least one energy storage unit configured to be charged to a first voltage from the input terminal, a sensing element configured to sense the environmental parameter, wherein the sensing element receives power from the at least one energy storage unit at a second voltage, and wherein the second voltage is lower than the first voltage, a controller configured to receive a sensor signal from the sensing element and to generate an output signal, and an output terminal configured to transmit output corresponding to the output signal. The input terminal may be a 4-20 mA input terminal, and the output terminal may be a 4-20 mA output terminal. The sensing unit may include a regulator coupleable between the input terminal and the at least one energy storage unit, the regulator configured to limit an input current received at the input terminal to a limited input current. The limited input current may be 4 mA. The regulator may be coupleable between the controller and the output terminal and may perform at least one current regulation operation in association with the output signal generated by the controller and provide the output corresponding to the output signal to the output terminal. The sensing unit may include a DC-DC conversion unit coupleable between the at least one energy storage unit and the sensing element, the DC-DC conversion unit being configured to convert the first voltage to the second voltage. The sensing unit may further include a current conversion unit coupleable to the input terminal and to the controller, the current conversion unit configured to generate the output corresponding to the output signal and to provide the output corresponding to the output signal to the output terminal. The second voltage may be an operational voltage associated with the sensing element. The input terminal and the output terminal may be configured to couple to a two-wire 4-20 mA current loop.

According to further aspects of the present disclosure, provided is a system for providing a sensor device. The system includes a control unit and a sensing unit coupleable to the control unit via a current loop. The sensing unit includes an input terminal coupleable to the current loop, at least one energy storage unit configured to be charged to a first voltage from the input terminal, a sensing element configured to sense an environmental parameter, wherein the sensing element receives power from the at least one energy storage unit at a second voltage, and wherein the second voltage is lower than the first voltage, a controller configured to receive a sensor signal from the sensing element and to generate an output signal, and an output terminal coupleable to the current loop and configured to transmit output corresponding to the output signal to the control unit via the current loop. The current loop may be a 4-20 mA current loop. The sensing unit may include a regulator coupleable between the input terminal and the at least one energy storage unit, the regulator configured to limit an input current received at the input terminal to a limited input current. The limited input current may be 4 mA. The regulator may be coupleable between the controller and to the output terminal and may be configured to perform at least one current regulation operation in association with the output signal generated by the controller and to provide the output corresponding to the output signal to the output terminal. The sensing unit may include a DC-DC conversion unit coupleable between the at least one energy storage unit and the sensing element, the DC-DC conversion unit configured to convert the first voltage to the second voltage. The sensing unit may include a current conversion unit coupleable to the input terminal and to the controller, the current conversion unit configured to generate the output corresponding to the output signal and to provide the output corresponding to the output signal to the output terminal, and further wherein the sensing unit is configured to transmit the output corresponding to the output signal to the control unit. The second voltage may be an operational voltage associated with the sensing element. The current loop may be a two-wire 4-20 mA current loop, and the input terminal and the output terminal may be communicatively coupleable to the control unit via the current loop.

According to still further aspects of the present disclosure, provided is a method for providing a sensor device. The method includes regulating an input current received at the sensor device below a threshold, charging an energy storage to a first voltage using the regulated input current, converting the first voltage to a second voltage, the second voltage being lower than the first voltage, powering a sensing element at the second voltage to obtain sensor data, generating an output signal corresponding to the obtained sensor data, selectively regulating the output signal to generate an output current, and transmitting the output current from the sensor device.

Numerous other objects, features, and advantages of the present invention will be readily apparent to those skilled in the art upon a reading of the following disclosure when taken in conjunction with the accompanying drawings.

BRIEF DESCRIPTION OF THE DRAWINGS

FIG. 4 illustrates an example of a process flow for providing a sensor device according to aspects of the present disclosure.

Figure 1:
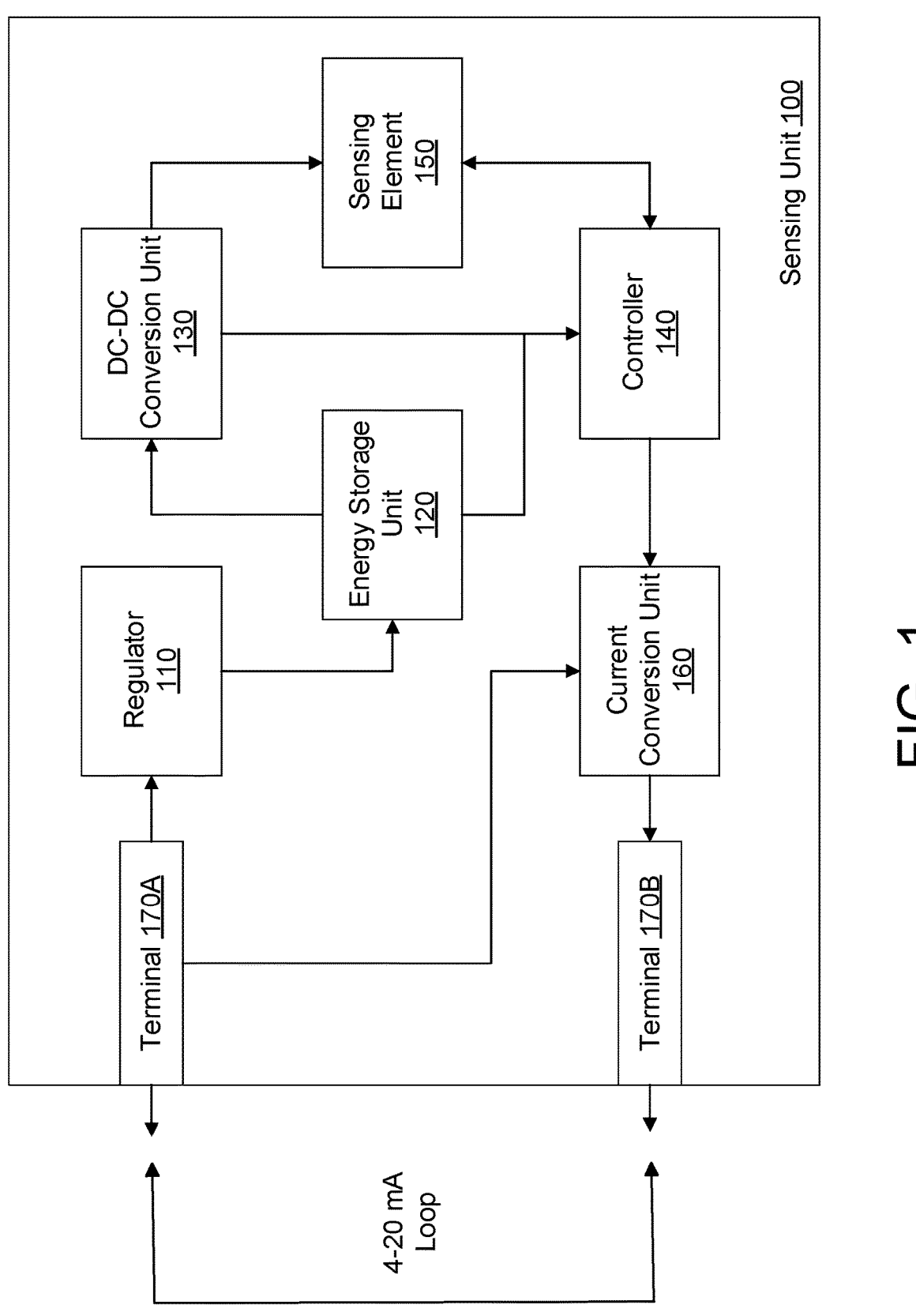
FIG. 1 illustrates a partial block diagram of an embodiment of a sensing unit according to aspects of the present disclosure.

A more detailed description of the disclosure, briefly summarized above, may be had by reference to various embodiments, some of which are illustrated in the appended drawings. While the appended drawings illustrate select embodiments of this disclosure, these drawings are not to be considered limiting of its scope, for the disclosure may admit to other equally effective embodiments.

Identical reference numerals have been used, where possible, to designate identical elements that are common to the figures. However, elements disclosed in one embodiment may be beneficially utilized on other embodiments without specific recitation.

DETAILED DESCRIPTION

FIG. 1 illustrates a partial block diagram of an embodiment of a sensing unit according to aspects of the present disclosure. A sensing unit 100 may be an environmental sensing device, such as an air quality (e.g., carbon dioxide ($CO_2$)) sensor. The sensing unit 100 may be useable with a Building Automation System (BAS), for example by communicating with a BAS controller (such as a control unit 210 described herein) which is coupleable to a current loop. For sensing units 100 functioning as a carbon dioxide ($CO_2$) sensor, the sensing units 100 may include a dual-beam, non-dispersive infrared (NDIR) technology, although other type of sensors and environmental sensing elements may be implemented by or in association with a sensing unit 100 without departing from the spirit and scope of the present disclosure. Although described with reference to two-wire configuration and operation of sensing units 100, it should further be appreciated that three-wire or additional implementations may be provided by the sensing unit 100, either in addition to or in the alternative to a two-wire configuration such as described herein.

The sensing unit 100 may include one or more of a terminal 170A (e.g., an input terminal), a regulator 110, at least one energy storage unit 120, a DC-DC conversion unit 130, a controller 140, a sensing element 150, a current conversion unit 160, and/or a terminal 170B (e.g., an output terminal). The sensing unit 100 is capable of coupling to one or more networks or devices, for example using one or more of the terminals 170A, 170B. In various embodiments, the sensing unit 100 is capable of coupling to a current loop via the terminals 170A, 170B. The current loop may be a 4-20 milliamp (mA) current loop or any other current loop capable of connecting to a sensing unit 100 and conveying one or more of power and/or control signals in relation to the sensing unit 100 or element associated therewith (e.g., control unit, Programmable Logic Controller (PLC), Supervisory Control and Data Acquisition (SCADA) system, etc.). The terminal 170A may be an input terminal and may be configured to couple connect to a power source wire of the current loop. The terminal 170B may be an output terminal and may be configured to connect to a read wire of the current loop. The terminals 170A, 170B may include screw terminals, for example configured to receive 18-24 American Wire Gauge (AWG) wires. The terminals 170A, 170B may be located at an external surface of a sensing unit 100 and/or may be housed within a housing of the sensing unit 100, either in whole or in part.

The sensing unit 100 includes a regulator 110 which is connected to the terminal 170A. The regulator 110 is configured to limit a current input to the energy storage unit 120. In various embodiments, the regulator 110 is a shunt regulator configured to limit input current to 4 mA. The input current limited by the regulator 110 is provided to the at least one energy storage unit 120. Although illustrated as a single energy storage unit 120, it should be appreciated that the energy storage unit may include a plurality of energy storage units 120 (e.g., as a capacitor bank or other configuration of a plurality of energy storage elements or units 120). The energy storage unit 120 is configured to charge to a charge voltage using the input current received from the regulator 110. In various embodiments, the energy storage unit 120 or element or attribute thereof may be selected or determined based at least in part upon an operational parameter of the sensing element 150. For example, charge parameter or storage parameter associated with the at least one energy storage unit 120 may be determined in whole or in part upon a peak current demand of the sensing element 150. The energy storage unit 120 may be connected to the controller 140 to provide a feedback signal. This may be done, for example, to provide feedback to the controller 140 on the input state of the power supply to ensure continuous operation of the sensing unit 100.

The energy storage unit 120 may be further connected to the DC-DC conversion unit 130. The DC-DC conversion unit 130 is configured to reduce a first voltage received from the energy storage unit 120 to a second, lower, voltage associated with the sensing element 150, and to provide the sensing element 150 with the second voltage which is lower than the first voltage. The DC-DC conversion unit is further connected to the controller 140 and to provide a third, lower, voltage to the controller 140, the third voltage associated with an operational voltage of the controller 140. The controller 140 is configured both to provide commands and signals to the sensing element 150 and to obtain sensor data from the sensing element 150. In various embodiments, the second voltage is the same as the third voltage.

The controller 140 may be a low power microcontroller or other hardware and/or software processor configured to perform one or more operations of or in association with the sensing unit 100 or element thereof. The controller 140 may be configured to control one or more operations of the sensing element 150, to obtain at least one set of data or information from the sensing element 150, and to generate and transmit an output signal (e.g., a Pulse Width Modulated (PWM) output signal relating at least in part to data or information obtained from or associated with the sensing element 150). This may include the controller 140 directing the sensing element 150 to obtain current sensing data, monitoring a power supply parameter as feedback from the energy storage unit 120 to permit continuous operation of the sensing unit 100, and generating an output signal including data or information relating to the current sensing data obtained by the sensing element 150. The output signal may be provided to the current conversion unit 160.

The current conversion unit 160 may be configured to generate an output in relation to the output signal obtained from the controller 140 (e.g., an output signal between 4-20 mA). The current conversion unit 160 may be used to adjust an output current of the sensing unit 100 at the terminal 170B based at least in part upon a current input at the terminal 170A so as to enable continuous operation even when a sensing element 150 of the sensing unit 100 draws more than 4 mA current. This is done by supplementing the fixed 4 mA input current provided by the regulator 110 with energy stored by the at least one energy storage unit 120 such that the stored energy of the at least one energy storage unit 120 ensures that the peak current demand of the sensing unit 100 of greater than 4 mA is satisfied while not drawing more than 4 mA from the 4-20 mA loop by the sensing unit 100. The current conversion unit 160 may be configured to provide a direct current (DC) current output to the terminal 170B.

Figure 2A:
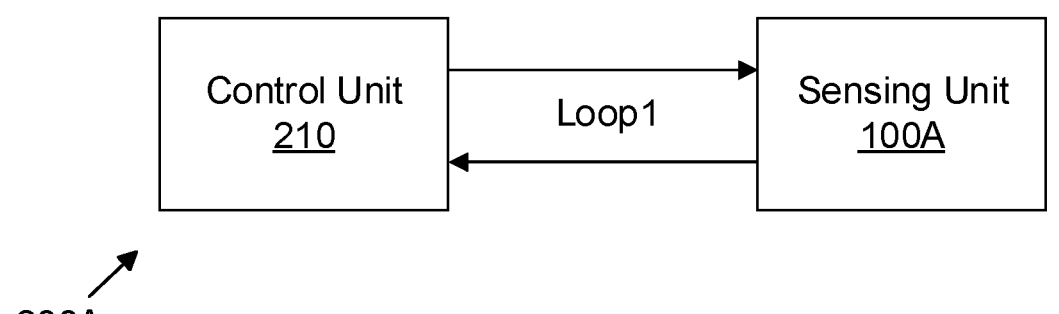
FIG. 2A illustrates a partial block diagram of an embodiment of a system for providing a two-wire sensor device according to aspects of the present disclosure.

FIG. 2A illustrates a partial block diagram of an embodiment of a system for providing a two-wire sensor device according to aspects of the present disclosure. The system 200A includes a sensing unit 100A coupled to a current loop, Loop1 (e.g., a 4-20 mA current loop), which is further coupled to a control unit 210. The control unit 210 may be a Building Automation and Control (BAC) controller or any device capable of controlling at least one sensing unit 100 and/or obtaining at least a portion of data or information relating to at least one sensing unit 100. The control unit 210 may be configured to provide power supply to the sensing unit 100 via the terminal 170A of the sensing unit 100 and to obtain data or information from the sensing unit 100 via the read wire via terminal 170B of the sensing unit 100. Although not illustrated, the control unit 210 may be communicatively couplable to a Building Management System (BMS), for example via one or more wired and/or wireless networks and protocols. The control unit 210 may be configured to receive commands or information from the BMS in relation to one or more sensing units 100 may further be configured to provide at least a portion of data or information associated with at least one sensing unit 100 to the BMS in various embodiments.

Figure 2B:
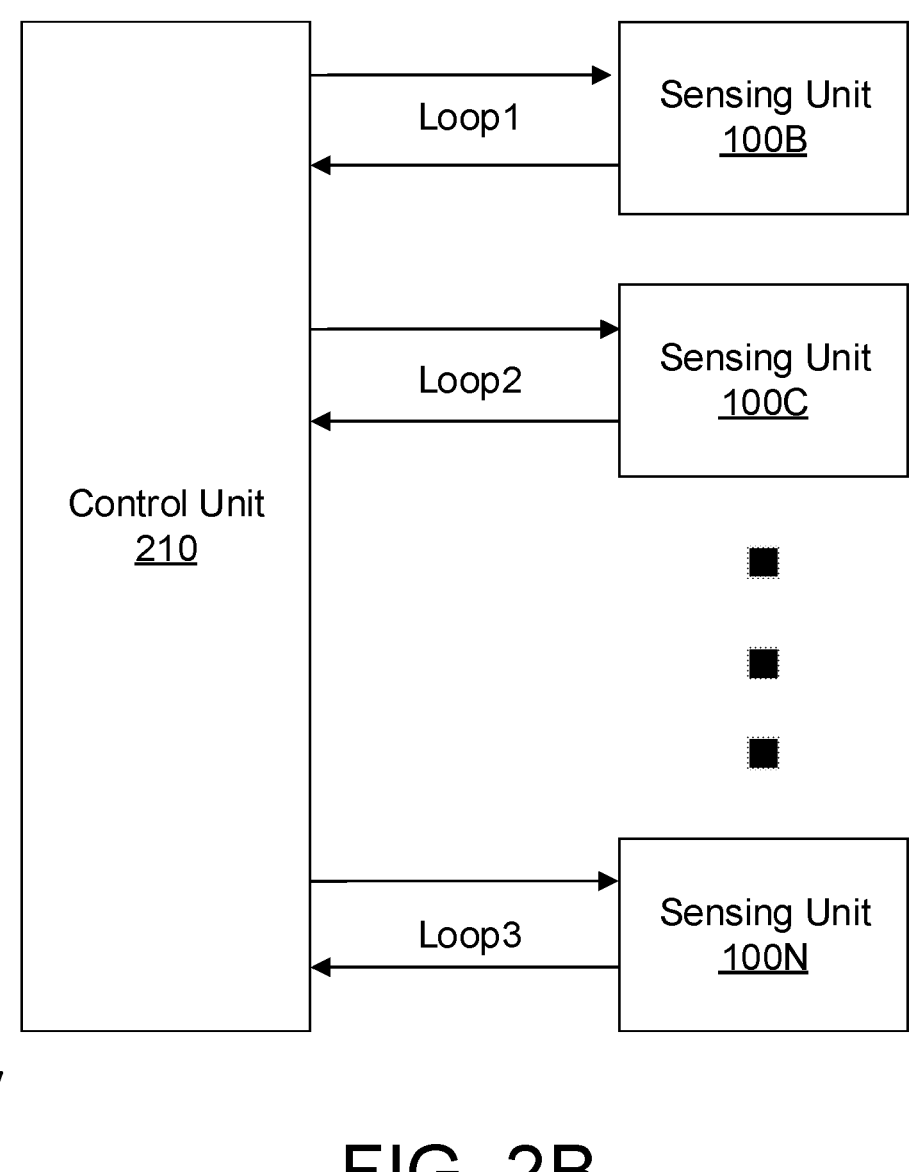
FIG. 2B illustrates a partial block diagram of an alternative embodiment of a system for providing a plurality of two-wire sensor devices associated with a control unit according to aspects of the present disclosure.

FIG. 2B illustrates a partial block diagram of an alternative embodiment of a system for providing a plurality of two-wire sensor devices associated with a control unit according to aspects of the present disclosure. The system 200B includes a plurality of sensing units 100B, 100C, . . . , 100N coupled to respective current loops, Loop1, Loop2, Loop3 (e.g., 4-20 mA current loops), which are further coupled to a common control unit 210. The control unit 210 may be a Building Automation and Control (BAC) controller or any device capable of controlling at least one sensing unit 100 and/or obtaining at least a portion of data or information relating to at least one sensing unit 100. The control unit 210 may be configured to provide power supply to the sensing units 100B, 100C, . . . , 100N via respective terminals 170A of the sensing units 100B, 100C, . . . , 100N and to obtain data or information from the sensing units 100B, 100C, . . . , 100N via the respective read wire via terminals 170B of the sensing units 100B, 100C, . . . , 100N. The control unit 210 may be configured to receive commands or information from the BMS in relation to one or more sensing units 100 may further be configured to provide at least a portion of data or information associated with at least one sensing unit 100 to the BMS in various embodiments.

Figure 3:
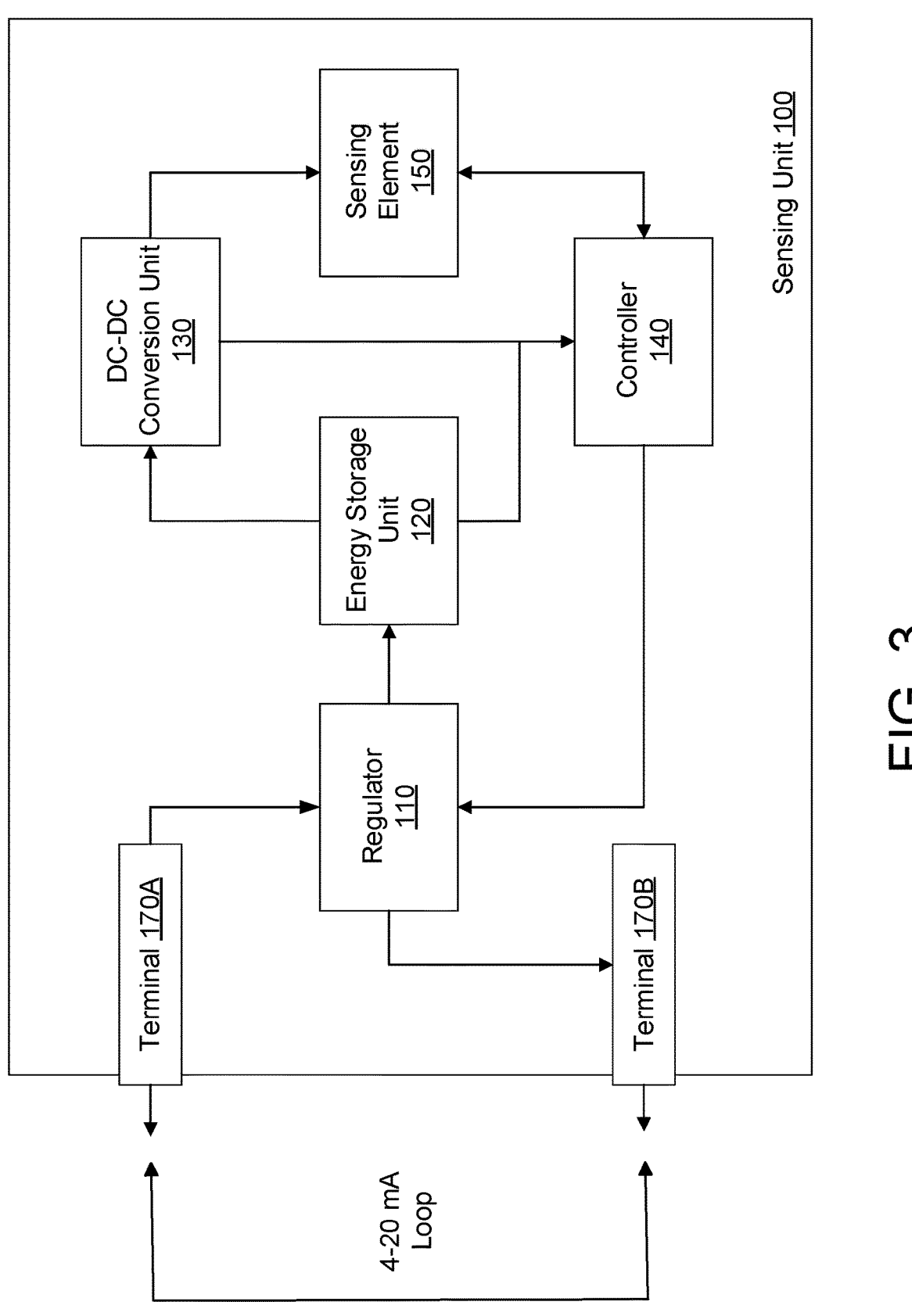
FIG. 3 illustrates a partial block diagram of an alternative embodiment of a sensing unit of FIG. 1 having a combined regulator according to aspects of the present disclosure.

FIG. 3 illustrates a partial block diagram of an alternative embodiment of a sensing unit of FIG. 1 having a combined regulator according to aspects of the present disclosure. The sensing unit 100 may be configured such that the regulator 110 is configured to perform functions previously described herein with reference to the current conversion unit 160. This may be accomplished by coupling the regulator 110 to the controller 140 to receive one or more signals from the controller 140, such as the output signal generated by the controller 140. The regulator 110 may thus be coupled to each of the terminals 170A, 107B, to the energy storage unit 120, and to the controller 140. The regulator 110 may be configured to generate an output in relation to the output signal obtained from the controller 140. The regulator 110 may be used to adjust an output current of the sensing unit 100 at the terminal 170B based at least in part upon a current input at the terminal 170A so as to enable continuous operation even when a sensing element 150 of the sensing unit 100 draws more than 4 mA current. This is done by supplementing the fixed 4 mA input current provided by the regulator 110 to the at least one energy storage unit with energy stored by the at least one energy storage unit 120 such that the stored energy of the at least one energy storage unit 120 ensures that the peak current demand of the sensing unit 100 of greater than 4 mA is satisfied while not drawing more than 4 mA from the 4-20 mA loop by the sensing unit 100. The regulator 110 may be configured to provide a direct current (DC) current output to the terminal 170B.

FIG. 4 illustrates an example of a process flow for providing a sensor device according to aspects of the present disclosure. The process 400 includes an operation 402 where a sensing unit 100 is coupled to a two-wire current loop (e.g., communicatively coupled to a control unit 210). An input current received at a power supply wire of the two-wire current loop is regulated at an operation 404, for example by regulator 110. The at least one energy storage unit 120 is selectively charged to a first voltage using the regulated input current at an operation 406. The first voltage is converted to a second voltage which is lower than the first voltage at an operation 408 (e.g., the second voltage based at least in part upon an operational parameter associated with the sensing element 150). The sensing element 150 is powered using the converted second voltage at an operation 410 to obtain sensor data. At least a portion of sensor data is provided to the controller 140 at an operation 412 and the controller 140 generates an output signal. Output from the sensing unit 100 is regulated (e.g., by a current conversion unit 160 and/or regulator 110) relating to the output signal generated by the controller 140 at an operation 414. The output from the sensing unit 100 relating to the output signal is transmitted at an operation 416.

Figure 5:
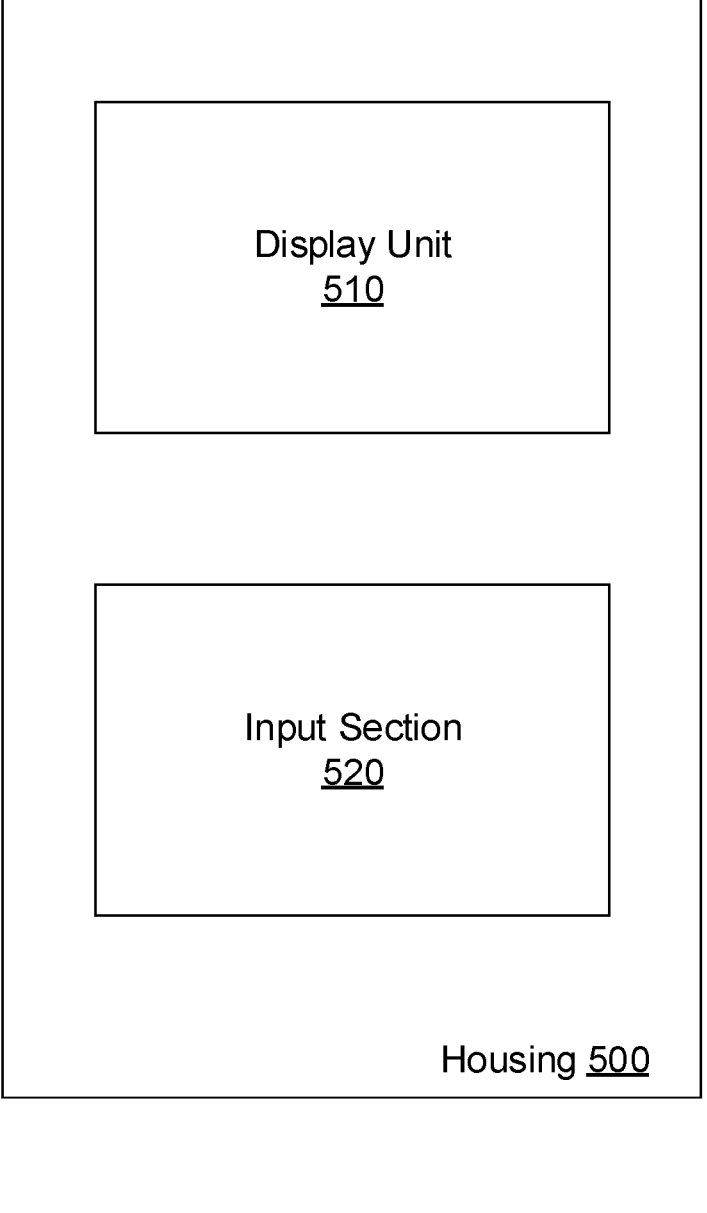
FIG. 5 illustrates a partial block diagram of an embodiment of a sensing unit according to aspects of the present disclosure.

FIG. 5 illustrates a partial block diagram of an embodiment of a sensing unit according to aspects of the present disclosure. A sensing unit 100 may include one or more of a display unit 510 and/or an input section 520 at a surface of a housing 500 of the sensing unit 100. The display unit 510 may be any medium capable of conveying information, such as a Liquid Crystal Display (LCD) or any other display type or format, or alternative means of conveying visual information. The display unit 510 may be powered by the sensing unit 100 and/or by a separate power source. Although described as a visual interface, it should be appreciated that any form of conveying information to a user may be used, for example, visual, audio, tactile, or any means of conveying information or combination thereof. At least one of the display unit 510 and/or input section 520 may be provided at any surface or location of the sensing unit 100. Additionally or alternatively, at least one of the display unit 510 and/or input section 520 may be coupleable to the sensing unit 100 and/or remotely located from the sensing unit 100 without departing from the spirit and scope of the present disclosure. The display unit 510 may be configured to visually convey at least one setting, parameter, operational value, or any other information associated with the sensing unit 100, control unit 210, building management system associated with the sensing unit 100 or control unit 210, or any other information which may be conveyed to a user of or other person or entity associated with the sensing unit 100. The input section 520 may include a touch screen, buttons, portal for connection, or any other means of obtaining input from a user or external element in association with the sensing unit 100.

In various systems, an air-quality-sensing system might need to power one or more $CO_2$ sensors with more than 4 mA in a respective 4-20 mA current loop but cannot draw more than 4 mA from an associated power supply when only two wires are connected to the sensing unit. One wire of the two-wire current loop may correspond to the power supply, while the second wire may be associated with the reading output. If more than 4 mA is drawn for a $CO_2$ sensor through the power-supply wire for a respective current loop, then more than 4 mA must be outputted through the respective reading-output wire. Implementations consistent with the present disclosure provide that the reading-output signal may be configured to remain independent of the current drawn by the sensor(s). Otherwise, a Building Automation System (BAS) receiving the reading output might be unable to differentiate the sensor reading from the current drawn by the sensor(s). In contrast to existing systems, implementations consistent with the present disclosure may enable powering sensing units with more than 4 mA in two-wire 4-20 mA systems without outputting more than 4 mA through the reading-output wire.

According to aspects of the present disclosure, provided is a sensing unit to sense an environmental parameter. The sensing unit may include an input terminal, at least one energy storage unit configured to be charged to a first voltage from the input terminal, a sensing element configured to sense the environmental parameter, wherein the sensing element receives power from the at least one energy storage unit at a second voltage, and wherein the second voltage is lower than the first voltage, a controller configured to receive a sensor signal from the sensing element and to generate an output signal, and an output terminal configured to transmit output corresponding to the output signal. The input terminal may be a 4-20 mA input terminal, and the output terminal may be a 4-20 mA output terminal. The sensing unit may include a regulator coupleable between the input terminal and the at least one energy storage unit, the regulator configured to limit an input current received at the input terminal to a limited input current. The limited input current may be 4 mA. The regulator may be coupleable between the controller and the output terminal and may perform at least one current regulation operation in association with the output signal generated by the controller and provide the output corresponding to the output signal to the output terminal. The sensing unit may include a DC-DC conversion unit coupleable between the at least one energy storage unit and the sensing element, the DC-DC conversion unit being configured to convert the first voltage to the second voltage. The sensing unit may further include a current conversion unit coupleable to the input terminal and to the controller, the current conversion unit configured to generate the output corresponding to the output signal and to provide the output corresponding to the output signal to the output terminal. The second voltage may be an operational voltage associated with the sensing element. The input terminal and the output terminal may be configured to couple to a two-wire 4-20 mA current loop.

According to further aspects of the present disclosure, provided is a system for providing a sensor device. The system includes a control unit and a sensing unit coupleable to the control unit via a current loop. The sensing unit includes an input terminal coupleable to the current loop, at least one energy storage unit configured to be charged to a first voltage from the input terminal, a sensing element configured to sense an environmental parameter, wherein the sensing element receives power from the at least one energy storage unit at a second voltage, and wherein the second voltage is lower than the first voltage, a controller configured to receive a sensor signal from the sensing element and to generate an output signal, and an output terminal coupleable to the current loop and configured to transmit output corresponding to the output signal to the control unit via the current loop. The current loop may be a 4-20 mA current loop. The sensing unit may include a regulator coupleable between the input terminal and the at least one energy storage unit, the regulator configured to limit an input current received at the input terminal to a limited input current. The limited input current may be 4 mA. The regulator may be coupleable between the controller and to the output terminal and may be configured to perform at least one current regulation operation in association with the output signal generated by the controller and to provide the output corresponding to the output signal to the output terminal. The sensing unit may include a DC-DC conversion unit coupleable between the at least one energy storage unit and the sensing element, the DC-DC conversion unit configured to convert the first voltage to the second voltage. The sensing unit may include a current conversion unit coupleable to the input terminal and to the controller, the current conversion unit configured to generate the output corresponding to the output signal and to provide the output corresponding to the output signal to the output terminal, and further wherein the sensing unit is configured to transmit the output corresponding to the output signal to the control unit. The second voltage may be an operational voltage associated with the sensing element. The current loop may be a two-wire 4-20 mA current loop, and the input terminal and the output terminal may be communicatively coupleable to the control unit via the current loop.

According to still further aspects of the present disclosure, provided is a method for providing a sensor device. The method includes regulating an input current received at the sensor device below a threshold, charging an energy storage to a first voltage using the regulated input current, converting the first voltage to a second voltage, the second voltage being lower than the first voltage, powering a sensing element at the second voltage to obtain sensor data, generating an output signal corresponding to the obtained sensor data, selectively regulating the output signal to generate an output current, and transmitting the output current from the sensor device.

In the preceding, reference is made to various embodiments. However, the scope of the present disclosure is not limited to the specific described embodiments. Instead, any combination of the described features and elements, whether related to different embodiments or not, is contemplated to implement and practice contemplated embodiments. Furthermore, although embodiments may achieve advantages over other possible solutions or over the prior art, whether or not a particular advantage is achieved by a given embodiment is not limiting of the scope of the present disclosure. Thus, the preceding aspects, features, embodiments, and advantages are merely illustrative and are not considered elements or limitations of the appended claims except where explicitly recited in a claim(s).

The various embodiments disclosed herein may be implemented as a system, method, or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer-readable medium(s) having computer-readable program code embodied thereon.

Any combination of one or more computer-readable medium(s) may be utilized. The computer-readable medium may be a non-transitory computer-readable medium. A non-transitory computer-readable medium may be, for example, but not limited to, an electronic, magnetic, optical, electromagnetic, infrared, or semiconductor system, apparatus, or device, or any suitable combination of the foregoing. More specific examples (a non-exhaustive list) of the non-transitory computer-readable medium can include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer-readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages. Moreover, such computer program code can execute using a single computer system or by multiple computer systems communicating with one another (e.g., using a local area network (LAN), wide area network (WAN), the Internet, etc.). While various features in the preceding are described with reference to flowchart illustrations and/or block diagrams, a person of ordinary skill in the art will understand that each block of the flowchart illustrations and/or block diagrams, as well as combinations of blocks in the flowchart illustrations and/or block diagrams, can be implemented by computer logic (e.g., computer program instructions, hardware logic, a combination of the two, etc.). Generally, computer program instructions may be provided to a processor(s) of a general-purpose computer, special-purpose computer, or other programmable data processing apparatus. Moreover, the execution of such computer program instructions using the processor(s) produces a machine that can carry out a function(s) or act(s) specified in the flowchart and/or block diagram block or blocks.

The flowchart and block diagrams in the Figures illustrate the architecture, functionality and/or operation of possible implementations of various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is to be understood that the above description is intended to be illustrative, and not restrictive. Many other implementation examples are apparent upon reading and understanding the above description. Although the disclosure describes specific examples, it is recognized that the systems and methods of the disclosure are not limited to the examples described herein but may be practiced with modifications within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

We claim:

1. A sensing unit to sense an environmental parameter, comprising:

an input terminal;

at least one energy storage unit configured to be charged to a first voltage from the input terminal;

a regulator coupleable between the input terminal and the at least one energy storage unit, the regulator configured to limit an input current received at the input terminal to a limited input current;

a sensing element configured to sense the environmental parameter, wherein the sensing element receives power from the at least one energy storage unit at a second voltage, and wherein the second voltage is lower than the first voltage;

a controller configured to receive a sensor signal from the sensing element and to generate an output signal; and an output terminal configured to transmit output corresponding to the output signal.

2. The sensing unit of claim 1, wherein the input terminal is a 4-20 mA input terminal, and further wherein the output terminal is a 4-20 mA output terminal.

3. The sensing unit of claim 1, wherein the limited input current is 4 mA.

4. The sensing unit of claim 1, wherein the regulator is further coupleable between the controller and to the output terminal and is configured to perform at least one current regulation operation in association with the output signal generated by the controller and to provide the output corresponding to the output signal to the output terminal.

5. The sensing unit of claim 1, further comprising:

a DC-DC conversion unit coupleable between the at least one energy storage unit and the sensing element, the DC-DC conversion unit configured to convert the first voltage to the second voltage.

6. The sensing unit of claim 1, further comprising:

a current conversion unit coupleable to the input terminal and to the controller, the current conversion unit configured to generate the output corresponding to the output signal and to provide the output corresponding to the output signal to the output terminal.

7. The sensing unit of claim 1, wherein the second voltage is an operational voltage associated with the sensing element.

8. The sensing unit of claim 1, where the input terminal and the output terminal are configured to be coupleable to a two-wire 4-20 mA current loop.

9. The sensing unit of claim 1, further comprising:

a housing for housing at least the at least one energy storage unit, the sensing element, and the controller.

10. The sensing unit of claim 9, wherein the input terminal and the output terminal are located at an external surface of the sensing unit or are housed within the housing either in whole or in part.

11. A system for providing a sensor device, the system comprising:

a control unit; and a sensing unit coupleable to the control unit via a current loop, the sensing unit including:

an input terminal coupleable to the current loop;

at least one energy storage unit configured to be charged to a first voltage from the input terminal;

a regulator coupleable between the input terminal and the at least one energy storage unit, the regulator configured to limit an input current received at the input terminal to a limited input current;

a sensing element configured to sense an environmental parameter, wherein the sensing element receives power from the at least one energy storage unit at a second voltage, and wherein the second voltage is lower than the first voltage;

a controller configured to receive a sensor signal from the sensing element and to generate an output signal; and an output terminal coupleable to the current loop and configured to transmit output corresponding to the output signal to the control unit via the current loop.

12. The system of claim 11, wherein the current loop is a 4-20 mA current loop.

13. The system of claim 11, wherein the limited input current is 4 mA.

14. The system of claim 11, wherein the regulator is further coupleable between the controller and to the output terminal and is configured to perform at least one current regulation operation in association with the output signal generated by the controller and to provide the output corresponding to the output signal to the output terminal.

15. The system of claim 11, wherein the sensing unit further includes a DC-DC conversion unit coupleable between the at least one energy storage unit and the sensing element, the DC-DC conversion unit configured to convert the first voltage to the second voltage.

16. The system of claim 11, wherein the sensing unit further includes a current conversion unit coupleable to the input terminal and to the controller, the current conversion unit configured to generate the output corresponding to the output signal and to provide the output corresponding to the output signal to the output terminal, and further wherein the sensing unit is configured to transmit the output corresponding to the output signal to the control unit.

17. The system of claim 11, wherein the second voltage is an operational voltage associated with the sensing element.

18. The system of claim 11, wherein the current loop is a two-wire 4-20 mA current loop, and further wherein the input terminal and the output terminal are configured to be communicatively coupleable to the control unit via the current loop.

19. A method for providing a sensor device, comprising:

regulating an input current received at the sensor device below a threshold, wherein the sensor device is coupled to a two-wire current loop;

charging an energy storage to a first voltage using the regulated input current;

converting the first voltage to a second voltage, the second voltage being lower than the first voltage;

powering a sensing element at the second voltage to obtain sensor data;

generating an output signal corresponding to the obtained sensor data;

selectively regulating the output signal to generate an output current; and transmitting the output current from the sensor device.

20. The method of claim 19, wherein the current loop is a 4-20 mA current loop.

\* \* \* \* \*